June 15, 1976
Y. YAMADA
NECTARINE TREE
Filed July 14, 1975
Plant Pat. 3,915
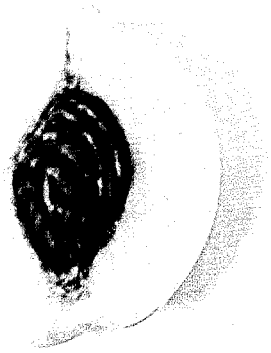
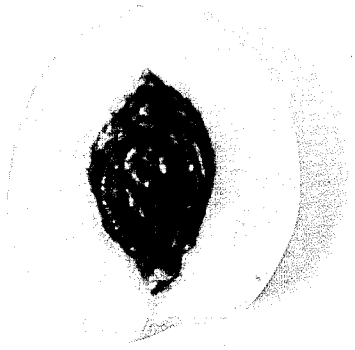
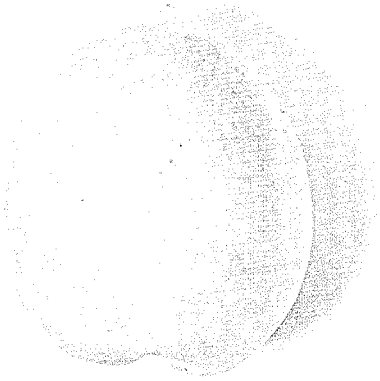
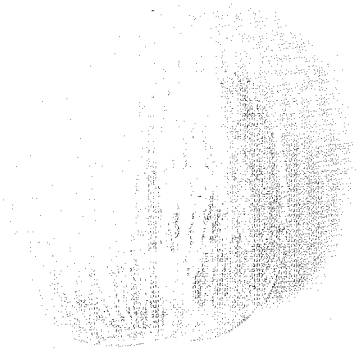

United States Patent

Plant Pat. 3,915

Patented June 15, 1976

3,915

NECTARINE TREE

Yoshio Yamada, Kingsburg, Calif., assignor to Vaughn Girazian, Fresno, Calif.

Filed July 14, 1975, Ser. No. 595,450

Int. Cl. A01h *5/03*

U.S. Cl. Plt.—41 1 Claim

ABSTRACT OF THE DISCLOSURE

A large, vigorous, productive nectarine tree which produces large, semi-cling, yellow-fleshed, yellow-skinned fruit, both moderately streaked with red, similar to the Autumn Grand Nectrine of U.S. Plant Pat. No. 2,894 in color but not as bright and ripening on or about October 1, three or four weeks later than the Autumn Grand. In shape, it is more like the Independence Nectarine (unpatented) but substantially larger.

BACKGROUND OF THE INVENTION

The perfection and improvement of fruit trees has progressed sufficiently that most kinds of fruit are available in a multiplicity of excellent varieties during their harvest seasons. Unfortunately, from the commercial grower's standpoint, the resultant competition frequently makes profitable operation impossible. As a consequence, the production of fruit at a time when there is a minimum of competition from other kinds of fruit and from other varieties of the same kind of fruit is of vital importance to the fruit farmer and beneficial to the consumer in the extension of the season.

ORIGIN

The subject variety nectarine tree was discovered by me growing in my orchard of Autumn Grand nectarines of U.S. Plant Pat. No. 2,894 at 14329 E. Nebraska, Kingsburg, Calif., where it attracted attention because of its extremely late ripening. It also attracted attention because of its vigorous growth and tendency to bear unusually large fruit unless thinned less than normal. It is believed to have originated as a sport of the Autumn Grand although it appeared as an entire tree in the orchard.

Upon discovery, in the new variety was carefully observed by me and, as soon as possible, I grafted it into other nectarine trees. The grafts flourished and were likewise carefully observed. Upon maturity, the progeny resulting from the grafts were found to possess the same characteristics as the original tree in all observable respects.

SUMMARY

The present new and distinct variety of nectarine tree is of vigorous growth, a regular bearer and of particular significance in its production of fruit which mature from September 25 to October 5, coincident with the ripening season of no other nectarines known to me. Its fruit are of excellent quality, of large size and good flavor, and of attractive appearance. The fruit is semi-cling, yellow-fleshed with a red blush and yellow-skinned with red streaks.

BRIEF DESCRIPTION OF THE DRAWING

The drawing is a photographic reproduction in color of two halves of two different nectarines of the instant variety cut on their suture planes with the pits remaining in place and having their exposed sides carefully cleaned of adherent flesh and fibers to reveal pit shape, structure and coloration and of two whole nectarines to show their external coloration.

VARIETAL DESCRIPTION

Referring in greater detail to the characteristics of the nectarine tree of the present invention, they are described generally in accord with the outline suggested by U. P. Hedrick in Systematic Pomology published in 1925 as observed under the ecological conditions prevailing in the County of Fresno, State of California and with color designations in accordance with the Nickerson Color Fan.

Tree generally:

*Size.*—Large, vigorous.

*Figure.*—Vase form, spreading.

*Productivity.*—Heavy.

*Regularity of bearing.*—Regular.

*Trunk.*—Size: Medium. Texture: Medium.

*Branches.*—Size: Medium.

*Leaves mature.*—Size: Normal for nectarines. Length: 16.5 cm. Width: 3.32 cm. Shape: Lanceolate with apex acuminate. Color: Moderate Olive Green, 2.5GY 4/3 to Moderate Yellow Green, 2.5GY 5/5. Marginal form: Minutely serrated. Petiole: Length—1.1 to 1.4 cm.; thickness—stout, .5 to .6 cm. Stem glands: Number—1 to 4; arrangement—alternate; size—medium; type—reniform. Stipules: Absent.

Flower buds: Medium size.

Flowers:

*Dates of bloom.*—Midseason.

*Size.*—Medium to large.

*Color.*—Pink.

Fruit:

*Maturity.*—September 25 to October 5, average October 1.

*Size.*—Large. Uniformity: Uniform. Diameter (length): 7 cm. to 7.6 cm. Diameter transverse in suture plane: 6.3 cm. to 6.9 cm. Diameter transverse at right angles to suture plane: 6 cm. to 6.6 cm.

*Form.*—Slightly elongated, globular, similar to the Independence Nectarine (unpatented) but larger. Uniformity: Consistent. Symmetrical or asymmetric: Relatively symmetrical. Suture: Shallow; length—from base to pistil point. Ventral surface; Rounded. Stem cavity: Deep 1.2 cm. to 2.5 cm. Base: Rounded. Apex: Rounded. Pistil point: Medium in size and sharply pointed.

*Skin.*—Thickness: Medium. Texture: Fine. Tendency to crack: Slight. Color: Vivid yellow 5Y 8/12 to 2.5Y 8/12, streaked with strong red 2.5R 5/12 to 5R 4/12.

*Flesh.*—Color: Brilliant yellow 5Y 9/9 streaked with strong red 5R 4/12. Surface of pit cavity: Deeply grooved. Color of pit well: Brilliant yellow 5Y 9/9 to strong red 5R 4/12 to brownish gray 10 YR 3/1. Juice: Abundant. Flavor: Tart. Aroma: Peach like. Texture: Fine. Ripening: Even. Eating quality: Excellent.

*Stone.*—Ovoid. Free or cling: Semi-cling. Fibers: Present, usually brilliant yellow 5Y 9/9. Size: 3.5 cm. long, 2.6 cm. wide, 1.9 cm. thick. Form: Symmetrical when viewed from side but asymmetrical when viewed from edge. Base: Slender and elongated. Sides: Asymmetrical. Ridges: Pronounced. Color: Strong red 5R 4/12 to strong brown 5YR 4/5. Splitting tendency: None observed. Use: Fresh, but too late for commercial drying. Keeping quality: Good. Shipping quality: Good when properly grown.

It is to be understood that the nectarine tree of the present invention is susceptible to the usual variations in growth rate, size, shape, productivity and ripening time normally caused by variations in soil, climate, irrigation frequency, and other environmental factors and cultural practices but is dependably of the described characteristics when subjected to good cultural practices and grown under the ecological conditions prevailing at the applicant's designated ranch in Fresno County, Calif.

What is claimed is:

1. A new and distinct variety of nectarine tree substantially as herein shown and described which bears large semi-cling yellow-fleshed and yellow-skinned fruit moderately streaked with red, similar to the Autumn Grand nectarine of U.S. Plant Pat. No. 2,894, in color but not as bright particularly characterized as to novelty by ripening from September 25 to October 5, three or four weeks later than the Autumn Grand.

No references cited.

ROBERT E. BAGWILL, Primary Examiner

UNITED STATES PATENT AND TRADEMARK OFFICE

CERTIFICATE OF CORRECTION

PATENT NO. : Plant Patent No. 3915

DATED : June 15, 1976

INVENTOR(S) : Yoshio Yamada assignor to Vaughn Girazian

It is certified that error appears in the above-identified patent and that said Letters Patent are hereby corrected as shown below:

Column 1, Line 14, delete "Nectrine" and insert --- Nectarine ---.

Column 1, Line 45, delete "in".

Signed and Sealed this

Twelfth Day of October 1976

[SEAL]

*Attest:*

RUTH C. MASON
*Attesting Officer*

C. MARSHALL DANN
*Commissioner of Patents and Trademarks*